US010820831B2

(12) United States Patent
Frank et al.

(10) Patent No.: US 10,820,831 B2
(45) Date of Patent: Nov. 3, 2020

(54) METHODS FOR MANUFACTURING CAPSULES WITH INGESTIBLE EVENT MARKERS

(71) Applicant: Proteus Digital Health, Inc., Redwood City, CA (US)

(72) Inventors: Jeremy Frank, San Francisco, CA (US); Nikhil Pargaonkar, Haywood, CA (US); Raymond Schmidt, San Francisco, CA (US); Robert Azevedo, Albany, CA (US); Kurt Scheinpflug, Fremont, CA (US); Nikolaus Leist, San Carlos, CA (US); Chris Dong, San Francisco, CA (US); Hiren Patel, Redwood City, CA (US); Peter Bjeletich, Livermore, CA (US); Robert Duck, San Francisco, CA (US)

( * ) Notice: Subject to any disclaimer, the term of this patent is extended or adjusted under 35 U.S.C. 154(b) by 408 days.

(21) Appl. No.: 15/794,084

(22) Filed: Oct. 26, 2017

(65) Prior Publication Data

US 2018/0110441 A1    Apr. 26, 2018

Related U.S. Application Data

(60) Provisional application No. 62/413,397, filed on Oct. 26, 2016.

(51) Int. Cl.
*A61B 5/07*    (2006.01)
*A61K 49/00*    (2006.01)
*A61K 9/48*    (2006.01)
*A61J 3/07*    (2006.01)
*A61J 3/10*    (2006.01)
*B30B 11/34*    (2006.01)
*B32B 37/14*    (2006.01)

(52) U.S. Cl.
CPC ............... *A61B 5/07* (2013.01); *A61B 5/073* (2013.01); *A61J 3/07* (2013.01); *A61J 3/074* (2013.01); *A61K 9/4808* (2013.01); *A61K 49/00* (2013.01); *B30B 11/34* (2013.01); *A61J 3/10* (2013.01); *A61J 2200/30* (2013.01); *A61J 2200/70* (2013.01); *B32B 37/14* (2013.01)

(58) Field of Classification Search
CPC .... A61B 5/073; A61B 5/07; A61J 3/07; A61J 3/074; A61J 3/10; A61J 2200/72; A61K 9/4808; A61K 49/00
See application file for complete search history.

(56) References Cited

U.S. PATENT DOCUMENTS

| 8,784,308 | B2 * | 7/2014 | Hafezi | ............ A61J 3/06 600/300 |
| 2002/0103425 | A1 * | 8/2002 | Mault | ............ A61B 5/0031 600/373 |
| 2002/0132226 | A1 * | 9/2002 | Nair | ............ A61B 5/0031 435/4 |

(Continued)

*Primary Examiner* — Jermie E Cozart

(57) ABSTRACT

Various methods and apparatuses are presented for an ingestible capsule that includes a digital, ingestible sensor component—or ingestible sensor—embedded into the capsule. The ingestible sensor component may be configured to activate upon coming into contact with conductive fluid, such as a body's stomach fluid. Once activated, the ingestible sensor component may be configured to perform various tasks, such as transmitting one or more signals and obtaining biometric data about the body that ingested the capsule.

11 Claims, 13 Drawing Sheets

(56) References Cited

U.S. PATENT DOCUMENTS

| | | | |
|---|---|---|---|
| 2003/0167000 A1* | 9/2003 | Mullick | A61B 1/00082 |
| | | | 600/424 |
| 2008/0281160 A1* | 11/2008 | Segawa | A61B 1/0011 |
| | | | 600/160 |
| 2013/0172694 A1* | 7/2013 | Zou | A61B 5/07 |
| | | | 600/302 |
| 2014/0275860 A1* | 9/2014 | Rottenberg | A61B 5/02042 |
| | | | 600/302 |
| 2016/0380708 A1* | 12/2016 | Dua | H04B 13/005 |
| | | | 375/219 |

* cited by examiner

METHODS FOR MANUFACTURING CAPSULES WITH INGESTIBLE EVENT MARKERS

CROSS REFERENCE TO RELATED APPLICATION

This application claims priority to U.S. Provisional Application 62/413,397, filed Oct. 26, 2016, and titled "METHODS FOR MANUFACTURING CAPSULES WITH INGESTIBLE EVENT MARKERS," the disclosure of which is hereby incorporated herein in its entirety and for all purposes.

BACKGROUND

Digital medicine typically includes an electronic sensor component closely associated with some application of medicine, and allows for improved data tracking, such as more accurate compliance and monitoring of various physiological signals. As the medical industry transitions into the age of digital medicine, practical challenges await, such as how to efficiently and reliably incorporate digital sensors into various medicines.

SUMMARY

Various methods and apparatuses are presented for an ingestible capsule that includes a digital, ingestible sensor component—or ingestible sensor—embedded into the capsule.

In some embodiments, a method of manufacturing an ingestible capsule including an ingestible sensor is presented. The method may include: accessing an already-manufactured ingestible capsule; and modifying the capsule to include an ingestible sensor using an automated manufacturing process, wherein the ingestible sensor includes a partial power source that powers the ingestible sensor when the partial power source comes into contact with a conductive fluid.

In some embodiments of the method, modifying the capsule to include the ingestible sensor using the automated manufacturing process comprises wedging the ingestible sensor into the capsule and affixing the ingestible sensor to the capsule using friction forces between edges of the ingestible sensor and an inner wall of the ingestible capsule, using the automated manufacturing process.

In some embodiments of the method, the ingestible sensor comprises at least a portion of material that is configured to flex or deform upon applying physical pressure, and wherein wedging the ingestible sensor into the capsule comprises flexing or deforming at least a portion of the ingestible sensor as the ingestible sensor is wedged into the capsule.

In some embodiments of the method, the material that is configured to flex or deform is insoluble and non-conductive and is further configured to magnify a signal emitted from the ingestible sensor by increasing a length of a current path formed between two dissimilar materials positioned on opposite sides of the ingestible sensor.

In some embodiments of the method, modifying the capsule to include the ingestible sensor using the automated manufacturing process comprises: affixing the ingestible sensor to a first band; forming an ingestible sensor band by affixing a second band over the ingestible sensor and the first band to sandwich the ingestible sensor in between the first band and the second band; and affixing the ingestible sensor band to the capsule by wrapping the ingestible sensor band around the capsule.

In some embodiments of the method, modifying the capsule to include the ingestible sensor using the automated manufacturing process comprises: embedding the ingestible sensor onto an inner wall of an outer cap; and affixing the outer cap over at least a portion of the capsule, such that the ingestible sensor is sandwiched between at least a portion of the capsule and the outer cap.

In some embodiments of the method, modifying the capsule to include the ingestible sensor using the automated manufacturing process comprises: securing an inner wall of the capsule using a support pin; on an outer wall of the capsule, opposite the inner wall of the capsule supported by the support pin, deforming a portion of the outer wall of the capsule to create a depression, using a deforming pin; and embedding the ingestible sensor into the depression of the outer wall.

In some embodiments of the method, modifying the capsule to include the ingestible sensor using the automated manufacturing process comprises: applying a glue material to an inner wall of the capsule; and securing the ingestible sensor to the inner wall of the capsule via the glue material. In some embodiments of the method, the glue material comprises at least one of: polyvinylpyrrolidone (PVP), hydroxypropyl cellulose (HPC), methylcellulose, ethylcellulose, gelatin or hydroxypropyl methylcellulose (HPMC).

In some embodiments of the method, modifying the capsule to include the ingestible sensor using the automated manufacturing process comprises: deforming a portion of the capsule by applying heat to the portion of the capsule; and attaching the ingestible sensor to the deformed portion of the capsule.

In some embodiments of the method, modifying the capsule to include the ingestible sensor using the automated manufacturing process comprises an ingestible sensor bead to the capsule using a fluid bed coating.

In some embodiments, another method of manufacturing an ingestible capsule including an ingestible sensor is presented. The method may include: partially forming the ingestible capsule using an automated manufacturing process; attaching the ingestible sensor to the partially formed ingestible capsule using the automated manufacturing process; and completing formation of the ingestible capsule, with the ingestible sensor included, using the automated manufacturing process, wherein the ingestible sensor includes a partial power source that powers the ingestible sensor when the partial power source comes into contact with a conductive fluid.

In some embodiments of the method, attaching the ingestible sensor to the partially formed capsule comprises wedging the ingestible sensor into a cap or partially formed body of the capsule, and affixing the ingestible sensor to the cap or partially formed body of the capsule using friction forces between edges of the ingestible sensor and an inner wall of the cap or partially formed body of the capsule.

In some embodiments of the method, the ingestible sensor comprises at least a portion of material that is configured to flex or deform upon applying physical pressure, and wherein wedging the ingestible sensor into the cap or partially formed body of the capsule comprises flexing or deforming at least a portion of the ingestible sensor as the ingestible sensor is wedged into the cap or partially formed body of the capsule.

In some embodiments of the method: partially forming the ingestible capsule comprises partially shaping capsule material using a forming pin; attaching the ingestible sensor to the partially formed capsule comprises: placing the ingestible sensor on a tip of the forming pin; and embedding the ingestible sensor into a rounded end of the partially formed capsule using the tip of the forming pin; and completing formation of the ingestible capsule comprises applying additional capsule material over the forming pin such that the ingestible sensor is attached via at least one surface of the additional capsule material that is not masked by the forming pin.

In some embodiments of the method, the ingestible sensor comprises a mating surface positioned opposite a side of the ingestible sensor adjacent to the rounded end of the capsule, the mating surface configured to mate with a drug component to be filled into the capsule.

In some embodiments of the method, the mating surface of the ingestible sensor comprises a concave shape.

In some embodiments of the method, the mating surface of the ingestible sensor comprises two straight edges connected at an acute angle.

In some embodiments of the method, attaching the ingestible sensor to the partially formed capsule comprises: coating a side of the ingestible sensor facing a distal end of the partially formed capsule with a material configured to accelerate separation of the ingestible sensor from the distal end of the capsule when the ingestible sensor is exposed to a fluid.

In some embodiments of the method, a portion of the capsule is constructed to be insoluble such that, when the capsule dissolves in a fluid, the insoluble portion of the capsule remains attached to the ingestible sensor and creates a skirt around the ingestible sensor.

In some embodiments of the method, attaching the ingestible sensor to the partially formed ingestible capsule using the automated manufacturing process comprises: casting a fast disintegrating layer of material into a distal end of the partially formed ingestible capsule; embedding the ingestible sensor onto the fast disintegrating layer of material; casting an insoluble layer of material onto the fast disintegrating layer and around the ingestible sensor; and casting a protective layer of material of material onto the insoluble layer and the ingestible sensor.

In some embodiments of the method, attaching the ingestible sensor to the partially formed capsule comprises: placing the ingestible sensor in a distal portion of the partially formed capsule; and completing formation of the ingestible capsule comprises crimping the partially formed capsule around the ingestible sensor such that the ingestible sensor is securely fastened within the distal portion of the capsule.

BRIEF DESCRIPTION OF DRAWINGS

Some embodiments are illustrated by way of example and not limitation in the figures of the accompanying drawings.

DETAILED DESCRIPTION

Figure 1:
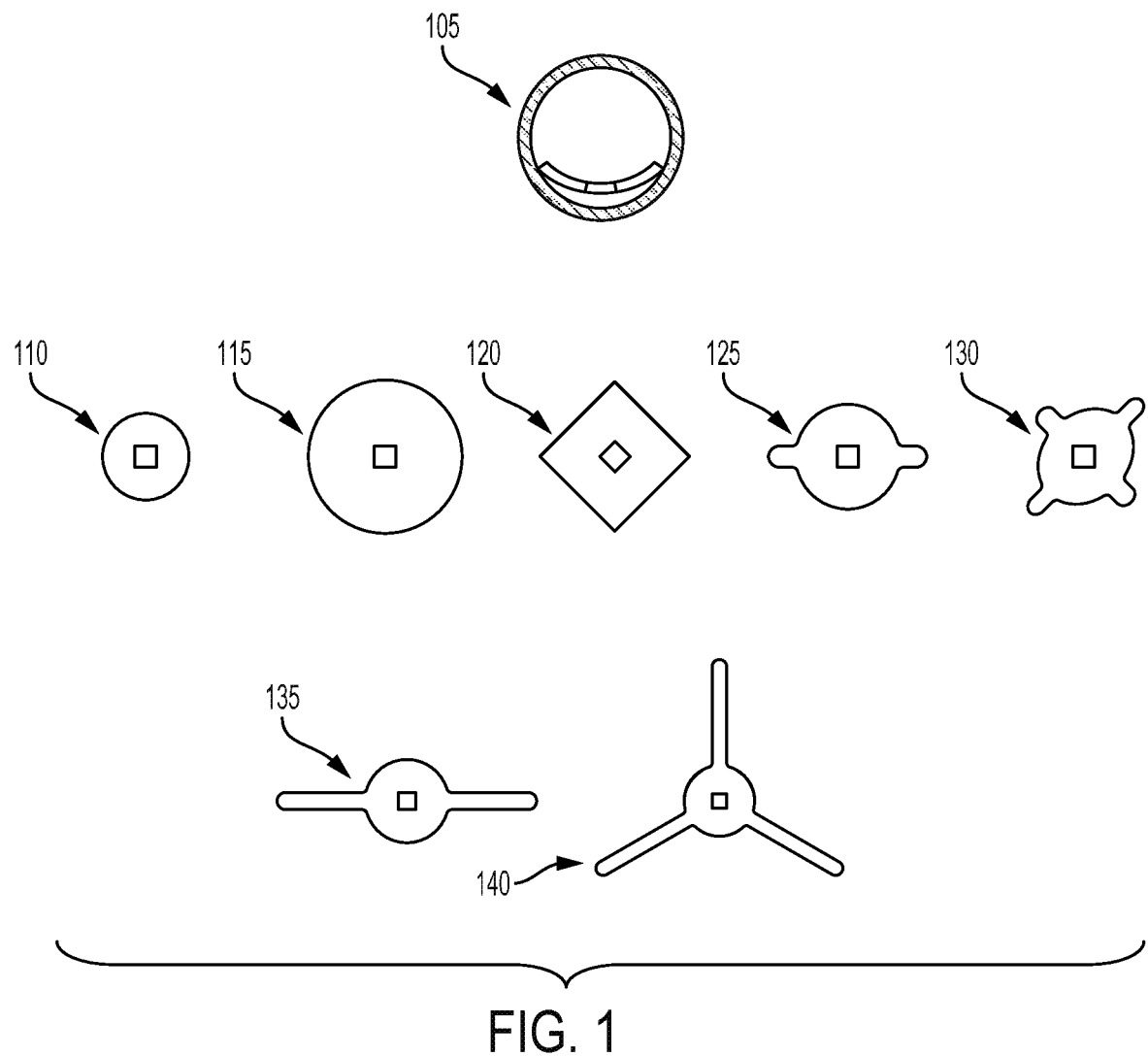
FIG. 1 illustrates various example geometries of a friction fit ingestible sensor package into a capsule.

In the following description, reference is made to the accompanying drawings that illustrate several embodiments of the present invention. It is understood that other embodiments may be utilized and mechanical, compositional, structural, and electrical operational changes may be made without departing from the spirit and scope of the present disclosure. The following detailed description is not to be taken in a limiting sense, and the scope of the embodiments of the present invention is defined only by the claims of the issued patent.

Various methods and apparatuses are presented for an ingestible capsule that includes a digital, ingestible sensor component—or ingestible sensor—embedded into the capsule. The ingestible sensor component may be configured to activate upon coming into contact with conductive fluid, such as a body's stomach fluid. Once activated, the ingestible sensor component may be configured to perform various tasks, such as transmitting one or more signals and obtaining biometric data about the body that ingested the capsule. Examples of an ingestible sensor component are an ingestible event marker (IEM) or a Mini-IEM Tablet (MIT). The ingestible sensor may also be referred to herein as a sensor pill (SP), IEM, and/or ingestible sensor microchip. The ingestible sensor includes a partial power source that is fully activated upon contact with a conductive fluid, and a circuit coupled to the partial power source and configured to perform one or more functions to transmit data through the body that ingested the capsule. As used herein, the process of including an ingestible sensor component into a capsule may be referred to as "digitizing" the capsule.

To improve mass production and manufacturing efficiency, it is desirable to create a stand-alone "digital" capsule that can then be used on standard pharmaceutical capsule-filling equipment to digitize any drug. Just placing an IEM in a capsule at the time of drug fill requires a custom piece of high-volume manufacturing equipment at every contract manufacturing organization (CMO) or partner that manufactures an encapsulated digital medicine. That approach can be expensive and may limit the number of CMOs that would be interested in manufacturing encapsulated digital medicines.

Simplistic methods for digitizing a capsule may create problems. For example, placing an ingestible sensor "loose" in a capsule may allow it to move around in an uncontrolled way that could impact device performance. In addition, loose ingestible sensors may also fall out of capsules during the encapsulation process causing product-quality concerns. The various embodiments of the present disclosures fix the ingestible sensor in a known and controlled location. Described below are a number of embodiments that may address how to digitize an ingestible capsule, particularly in accordance with known manufacturing techniques for creating ingestible capsules in general.

As described, some of the example methods provide manufacturing processes for including the ingestible sensor with a capsule after the capsule has already been manufactured, i.e., post-capsule manufacturing. These methods may be used to modify existing capsules using an additional automated manufacturing process that utilizes existing capsule manufacturing processes. Also described are some example methods for utilizing a single manufacturing process that includes the ingestible sensor with a capsule during the capsule manufacturing.

Friction Fit Ingestible Sensors

In some embodiments, an ingestible sensor is inserted in a capsule in such a way that it is held in place by deforming some portion of the ingestible sensor and/or the capsule cap or body itself. This "friction fit" is sufficient to keep the ingestible sensor in the capsule during all the downstream shipping and manufacturing steps to make a digital medicine.

The geometry of the ingestible-sensor skirt can be modified to create features that flex or deform as part of the insertion process used to place the ingestible sensor in the capsule. Those features could include adding "corners," "feelers," or simply making the ingestible-sensor skirt larger than the inner dimension of the capsule cap or body. In general, the skirt around the ingestible sensor is made of insoluble, non-conductive material that effectively amplifies the signal being transmitted from the ingestible sensor. The ingestible sensor typically creates a signal by modulating a current formed by the conductive fluid connecting two dissimilar materials located on opposite sides of the ingestible sensor. The length of the current path is increased using the skirt material, thereby increasing the strength of the signal formed by the current path. Here, the skirt material may also be used to provide friction to securely wedge the ingestible sensor into the capsule. The same insoluble, non-conductive material may also be flexible or deformable to a degree to allow bending that increases the forces of friction. FIG. 1 illustrates various example geometries of a friction fit ingestible sensor package into a capsule. Diagram 105 shows an example of a cross-sectional area of a capsule with an ingestible sensor wedged into one side of the capsule. As shown, the ingestible sensor in this case is bent or deformed partially, to fit into a side of the capsule. This "friction fit" may help maintain an ingestible sensor to stably stay in the capsule, and prevent loss during supply chain or manufacturing activities.

Ingestible sensors 110, 115, 120, 125, 130, 135, and 140 show additional examples of geometries that may be used to provide a "friction fit" into the capsules. The center module shown in each of the examples shows where the ingestible sensor may be placed, while the material around the ingestible sensor represents a skirt material that is insoluble and may be used to enhance the signal transmission capabilities when the ingestible sensor is activated. Ingestible sensor 110 shows a standard size sensor. Ingestible sensor 115 shows an "oversized" sensor with a large skirt. Ingestible sensor 120 shows a rhombus shaped skirt. Ingestible sensor 125 shows a double-lobed skirt, while ingestible sensor 130 shows four lobes around the skirt. Ingestible sensor 135 shows two long arms of the skirt in a "feeler" configuration, that may be used to deter the ingestible sensor from getting wedged to a side wall of the stomach or other area where conductive fluid is needed to reach opposite sides of the ingestible sensor. The sensor 140 includes a triple arm configuration for the skirt, to further enhance these capabilities. The "friction fit" method may be used both during a manufacturing process that integrates the ingestible sensor pill or tablet into the capsule during the capsule manufacturing process, and post-process of capsule manufacturing, i.e., modifying an existing capsule to include the ingestible sensor.

Though aspects of the present disclosure are applicable to ingestible sensors placed in the capsule body or cap, placing the ingestible sensor in the cap of a capsule may reduce the risk of the ingestible sensor interfering with the drug blend or tablet that is placed in the body of the capsule during the encapsulation process. The capsule material may act as a barrier between the drug blend/pellets and the IEM.

Ingestible Sensor Capsule Band

Figure 2:
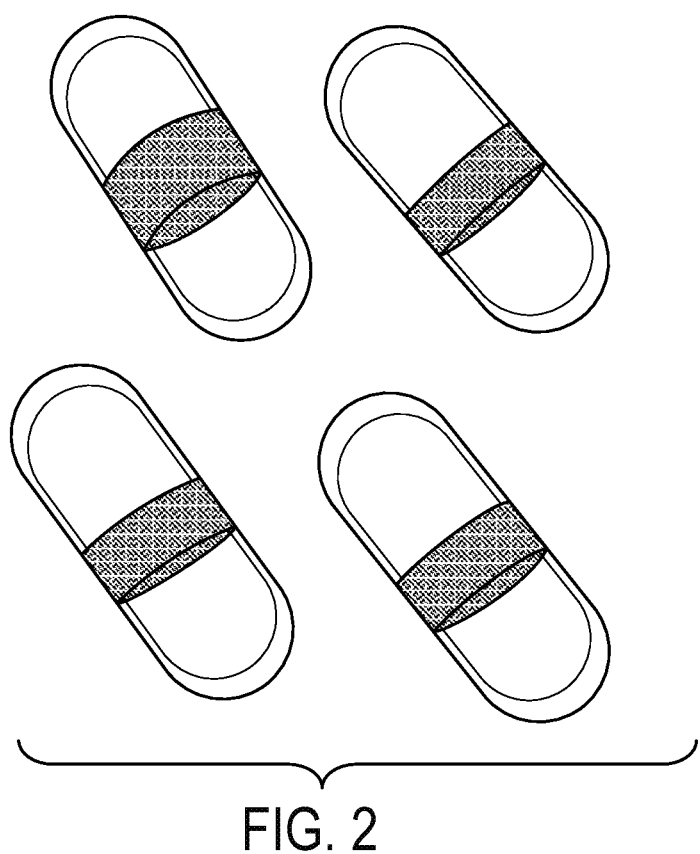
FIG. 2 shows an illustration of capsules having a band around them.

In some embodiments, an ingestible sensor may be placed within a band that encapsulates the body of a capsule. FIG. 2 shows an illustration of capsules having a band around them. The ingestible sensor may be manufactured to fit within the band. Example processes for creating a band are known, such as the Quali-seal process originally developed by Shionogi, Capsugel processes, or R. P. Scherer Hardcapsule processes. The bands being included around a capsule may be an example of adding the ingestible sensor post-capsule manufacturing. Further, this may be an example where no mechanical change to the capsule itself is required. This may allow for certain capsules to be more easily retrofitted to include ingestible sensors, and/or allow for certain capsule manufacturing processes to easily integrate ingestible sensors.

Figure 3:
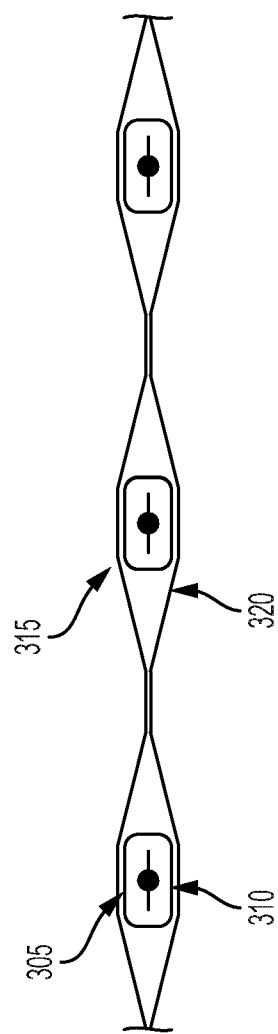
FIG. 3 shows a diagram of how the IEM may be included into a banding ribbon.

FIG. 3 provides an example for how to include the ingestible sensor into the band, a band ribbon of IEMs is created using standard film lamination techniques. The IEM 305 is sandwiched in between the band layers 315 and 320. Additionally, materials, such as loose or compacted materials 310, may be added around the IEM 305 to enhance IEM detachment upon contact with fluids. The band may be compatible with existing banding equipment. A standard roll-to-roll web-processing manufacturing tool can be used to create the banding ribbon. This process is typically performed by an automated machine that can precisely and quickly assemble these components. This process may allow for the adding of the ingestible sensor post-capsule manufacturing.

In this way, existing techniques for developing and filling capsules may not need to be modified in order to incorporate an ingestible sensor. This process may then be applied to any capsule that the band may fit around, increasing the universality of inclusion of the ingestible sensor.

Molded Sensor-to-Capsule Attach Method

In some embodiments, an IEM or Sensor Pill (SP) (e.g., IEM in placebo tablet) is molded into a capsule in such a way that it is held in place via drying or curing of the capsule material in direct contact with the sensor device during the capsule forming process. This method of attachment is sufficient to keep the IEM/SP in the capsule during all the downstream shipping and manufacturing steps to make a digital medicine and to maintain a unique orientation relative to the capsule and the subsequent drug load. The construction materials for the sensor pill can be chosen to not only optimize the coating process and adhesion between sensor pill and capsule, but also to optimize the sensor performance based on capsule material of construction (e.g., gelatin, hydroxypropyl methylcellusose, or carrageenan). For example, choice of binders or disintegrants may assist with separation of capsule and sensor in the stomach.

Figure 4A:
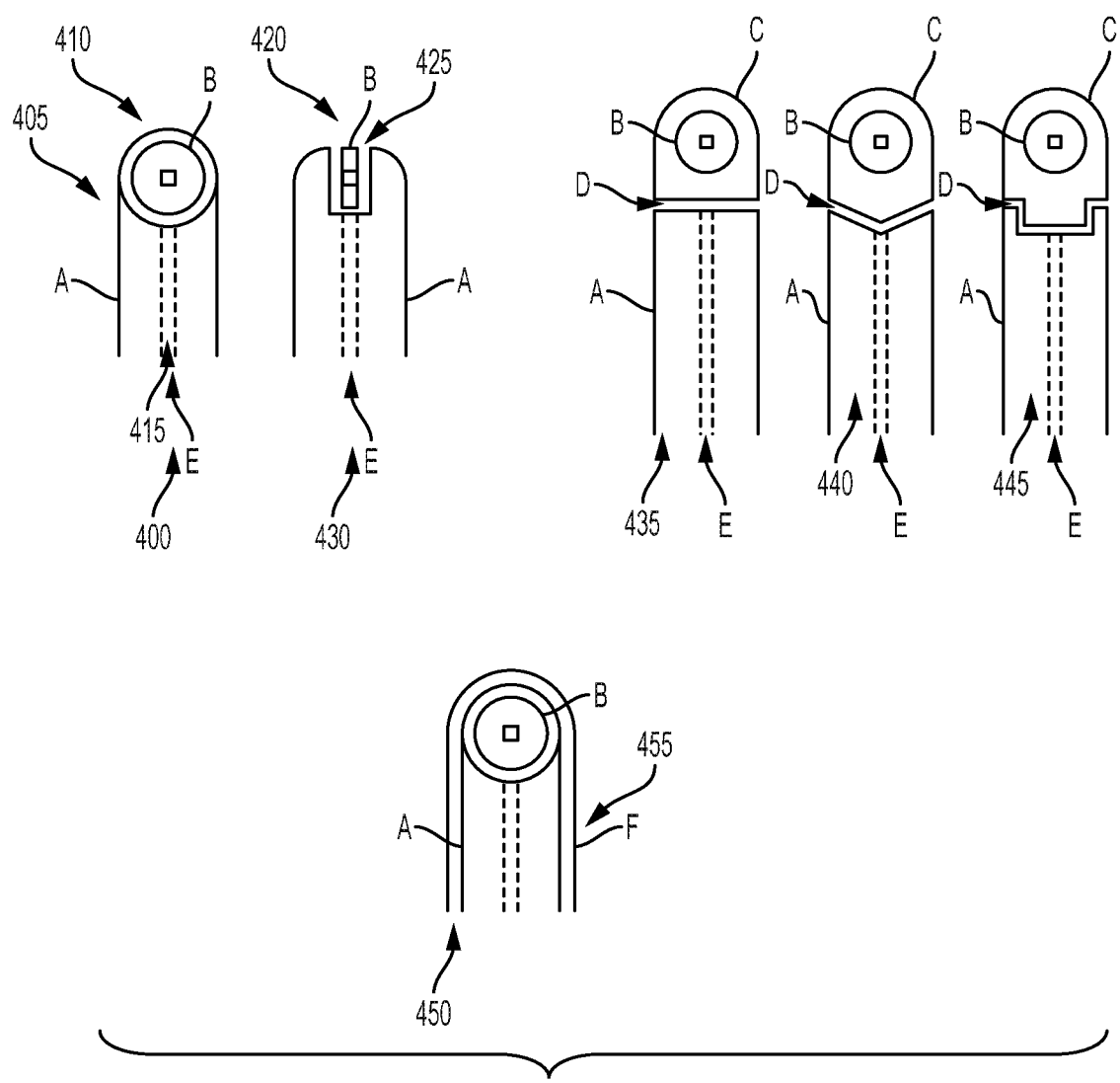
FIGS. 4A-4B illustrate a number of variations for how an ingestible sensor may be molded into a capsule.
Figure 4B:
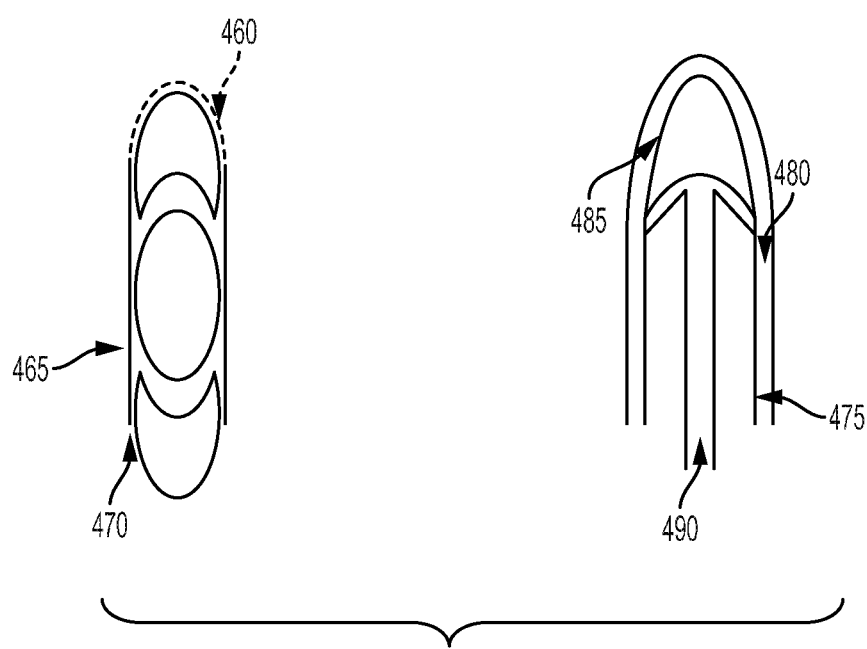

FIGS. 4A and 4B illustrate a number of variations for how an ingestible sensor may be molded into the capsule. As an example process consistent with FIG. 4A for molding the IEM into the capsule, illustration 400 shows a front view of a process for forming the capsule with an IEM using a forming pin 405, while illustration 430 shows a side view of the same. The capsule forming pin 405 would have a vertical channel machined into the rounded tip 410 in a shape to accommodate the IEM 420 held vertically. Prior to applying the capsule material to the forming pin 405, an IEM 420 is placed into the vertical channel 425 such that the circumference of the IEM 420 is approximately flush with the radius of the rounded tip 410. A small vacuum port 415 may be included within the forming pin 405 to help keep the IEM 420 in place. Capsule material 455 is then applied over the pin holding the IEM such that the outer surface is smooth and the IEM is intimately attached around the portion of its edge that was exposed (see illustration 450).

As an example process consistent with FIGS. 4A and 4B for molding the sensor pill into the capsule, the rounded tip of the forming pin is replaced with a tip geometry that mates with one surface of the sensor pill. The mating surface of the sensor pill can be flat (see illustration 435), shaped to enhance capsule forming process (see illustrations 440 and 445), or concave to allow for greater tablet volume of the finished digital capsule. The non-mating surface(s) of the sensor pill can be shaped to mimic the rounded end of a standard capsule (useful for taking advantage of standard capsule filling equipment), have custom geometry to differentiate the capsule as having a digital element, or have more pronounced taper for enhanced swallowability. Capsule material is then applied over the pin holding the sensor pill such that the outer surface is smooth and the sensor pill is intimately attached via the surface(s) that were not masked by the forming pin.

FIG. 4B shows an example of an assembled digital capsule with the sensor pill 460 attached to one end of the drug tablet 465. In this example, the mating surface connecting to the drug tablet is shaped in a concave manner. The sensor pill 460 and drug tablet 465 combination may then be coated to encase the entire combination. In this example, a second sensor pill 470 is connected to the opposite end of the drug tablet 465 for increased power and functionality. To form the tapered capsule, as shown, a forming pin 475 may be used to press the sensor pill 485 into a defined shape, in combination with a vacuum port 490. The drug tablet may then be pressed against the sensor pill at the mating surface. The capsule material 480 covers the combination of the different components.

If the forming pin must be dipped into solution of capsule material, the IEM or sensor pill can be held in the forming pin via the application of very slight vacuum. Alternatively, the capsule can be formed via spray coating capsule material onto forming pin with IEM or sensor pill in upright position (see FIGS. 4A and 4B).

The described techniques for forming capsules to sensor are applicable to both the cap and body portion of the capsule.

In this way, the molded process may allow for a single step manufacturing process (i.e., no secondary process to attach sensor after capsule is formed). In addition, the formulation of the molded process fixes orientation of the sensor within the capsule for predictable sensor performance, fixes orientation of the sensor within capsule body for consistent filling of drug contents (i.e., movement of sensor is impeded to eliminate potential air pockets that could not fill with drug), and fixes sensor to capsule such that it is not dislodged/removed during drug filling of the capsule.

Double Capsule with Ingestible Sensor

In some embodiments, the ingestible sensor may be included into a capsule by designing the empty capsules with two caps, of which one (inner) will fit inside the second (outer) cap to form a snug fit and leaving enough space for the IEM or sensor pill to be placed between the caps. The top portion of the inner cap may be shaped slightly flat to accommodate the IEM or sensor pill placement.

Figure 5:
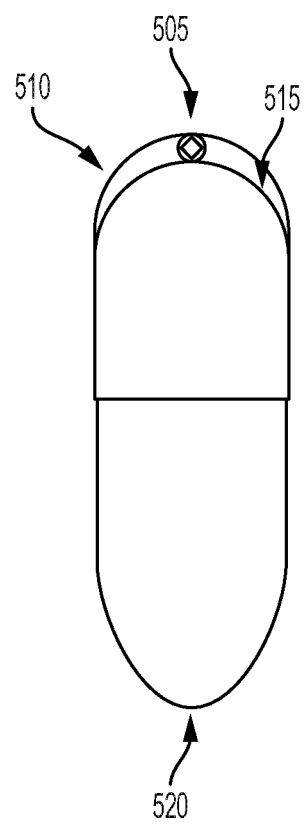
FIG. 5 provides an example of a double cap capsule that includes the ingestible sensor.

FIG. 5 provides an example of a double cap capsule that includes the ingestible sensor. The IEM or sensor pill 505 may be placed inside the outer cap 510 first, then the inner cap 515 may be fit snugly into the outer cap, securing the IEM or Sensor Pill 505. The capsule filling and formulation process may then proceed as normal in accordance with desired manufacturing techniques, until the rest of the body 520 of the capsule is formed. Placing the ingestible sensor in between the two caps of a capsule reduces the risk of the ingestible sensor interfering with the drug blend or tablet that is placed in the body of the capsule. This is another example of including the IEM or sensor pill to the capsule post-capsule manufacturing, and without requiring a mechanical modification to the existing capsule.

Sensor-to-Capsule Wall Attach Methods

In some embodiments, an IEM or sensor pill is lodged into the wall of a capsule via one of the following methods:
Casting or molding during capsule forming;
Pressure and/or temperature attachment;
Press fit into hole punched in capsule; and
Adhesive fixed into hole punched in capsule.

Figure 6:
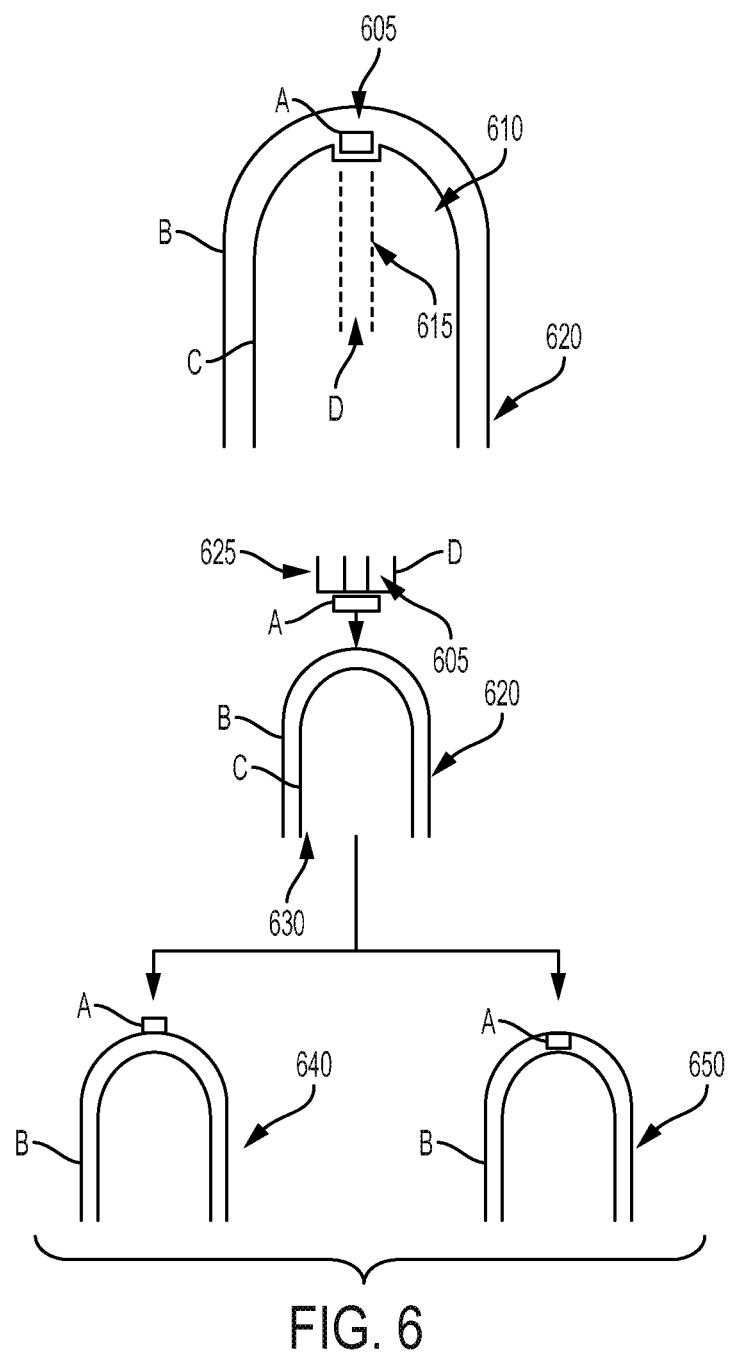
FIG. 6 provides various illustrations of the different formulations for including the IEM or other ingestible sensor into a capsule wall.

FIG. 6 provides various illustrations of the different formulations for including the IEM 605 or other ingestible sensor into a capsule wall. The portion of the capsule wall into which the IEM circuit is fixed may include standard capsule materials 620 or materials for enhanced function of the IEM circuit (e.g., material composition similar to the existing IEM skirt for signal strength enhancement).

In embodiments in which one electrode face of the IEM integrated circuit is in contact with the capsule wall, a coating can be applied to the IEM electrode face prior to attaching to the capsule to aid in affixing the IEM circuit to the wall and/or accelerate the separation of IEM circuit and capsule material when exposed to aqueous/acidic conditions like those present in the stomach.

In some embodiments, for casting/molding during capsule forming, a depression with shape similar to IEM circuit may be placed on an end of a forming pin 610. The IEM circuit 605 may be placed in a depression via vacuum pick-and-place. Positioning/hold of the circuit may be assisted via a vacuum port 615 on the forming pin 610. Capsule material is then formed on the pin via dip coating, spray coating, or other deposition techniques. A capsule with the IEM circuit is then removed from the forming pin. Multiple IEM circuits may be placed in both the body and cap portion of capsule for redundant signal transmission.

In some embodiments, for pressure/temperature attach methods, the IEM circuit 605 may be pressed against the wall of capsule via pick-and-place tip 625 capable of applying enough heat or pressure to affix the circuit to the wall. The pick-and-place tip 625 may be pressure based or temperature based. During application of heat and/or pressure, the capsule wall 620 may deform and thin next to the circuit electrode surface being pressed against the capsule. A support pin 630 may provide definition to the capsule wall 620 as the IEM 605 is being pressed into the capsule wall 620. Heat may be applied via conduction from the place tip 625 or via a non-contacting method (e.g. convective, radiative heating). Illustration 640 shows an example of the placement of the IEM onto the capsule with low temperature or pressure applied, while illustration 650 shows an example of the placement of the IEM onto the capsule with high temperature or pressure applied.

In some embodiments, for press fit attach methods, a hole with slightly smaller dimensions than the IEM integrated circuit is punched into any surface of capsule. The IEM circuit is then placed into the hole via pick-and-place tip that applies enough pressure to push the circuit to sit flush in the capsule wall.

In some embodiments, for adhesive attach methods, a hole is punched into any surface of the capsule. The hole size can range from slightly undersized (creating friction fit to assist in hold) to slightly oversized (allowing for separation between circuit and wall or space for adhesive to fill in for better hold). The IEM circuit is then placed in the hole via pick-and-place manufacturing operations. Adhesive is then applied either around edges of circuit or as a drop covering entire surface of circuit. Adhesives used may be set via drying, curing, cross-linking, or other means of action.

In some embodiments, a portion of the capsule wall that connects to the ingestible sensor may be constructed to be insoluble. This portion may be shaped in a way so as to add wings or a skirt around the ingestible sensor. Thus, when the capsule wall dissolves, the insoluble skirt and ingestible sensor will remain, and the skirt may amplify the reach of the ingestible sensor signal when activated.

Pick-and-place tips for circuit handling may be based on vacuum hold or mechanical grip and may include functionality to simultaneously place circuit and apply heat, pressure, or adhesive.

By employing any of these example methods for placing the ingestible sensor into the capsule wall, the orientation of the sensor on capsule wall may be fixed to create predictable sensor performance. In addition, there may be less occlusion of internal capsule volume allowing for maximum volume of drug product to be filled in a given capsule size. Also, these methods may fix the sensor to the capsule such that it is not dislodged/removed during drug filling of the capsule. These examples associated with FIG. 6 are other examples of integrating the IEM or sensor pill into the capsule during the capsule manufacturing process. Alternatively, embedding the IEM or sensor pill in the ways described associated with FIG. 6 may occur post-capsule manufacturing. For example, an additional process of creating a hole through a portion of an existing capsule to embed the IEM or sensor pill may occur.

Digital Capsule with Glued or Mold Casted Sensor

Since gelatin or hydroxypropylmethylcellulose are the most common materials used for capsules, choices are limited, so there is a need to tailor the ingestible sensor such that it would function well in these types of capsules. The glue or casting material is one which would hold the die (ingestible sensor microchip), IEM, or sensor pill in place within the capsule shell. The glue or casting material composition could be, but is not limited to, polyvinylpyrrolidone (PVP), hydroxypropyl cellulose (HPC), methylcellulose, ethylcellulose, gelatin or hydroxypropyl methylcellulose (HPMC).

In some embodiments, a die, IEM, or sensor pill is attached to a location inside a capsule shell held by a glue or casting material. This digitized capsule then allows for downstream shipping and manufacturing steps to make a digital medicine capsule product.

FIGS. 7A-7D illustrate various embodiments for how the ingestible sensor may be attached to the capsule 715 via glue or casting material 705. In case of glue or casting material 705, it hardens, cures or dries such that it holds the die (ingestible sensor microchip) 710, ingestible sensor, or sensor pill in place. In the case of the casting material, it could act as a skirt to enhance the sensor performance.

Figure 7A:
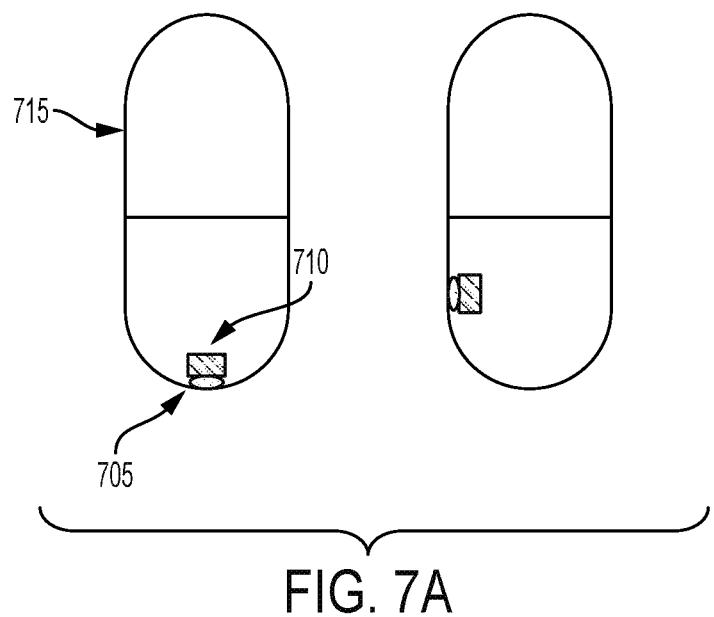
FIGS. 7A-7D provide examples of a digitized capsule using molded or casted methods.
Figure 7B:
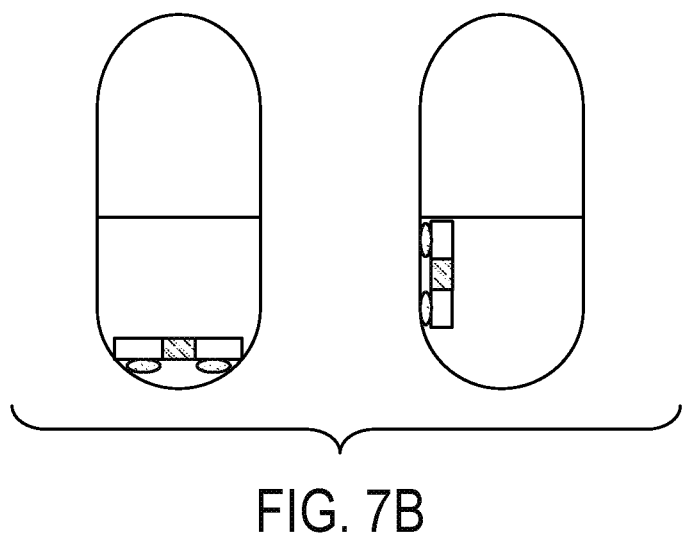
Figure 7C:
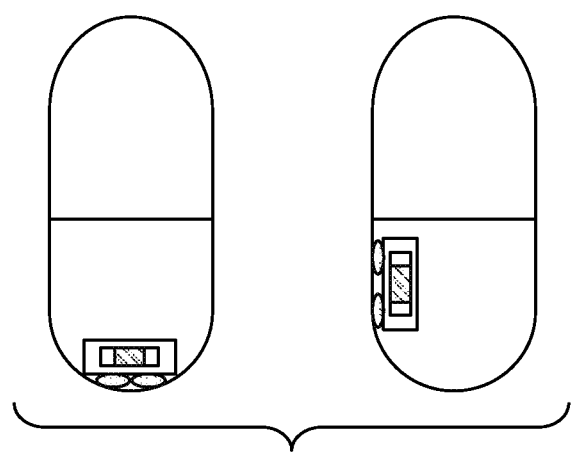

In some cases, the glue material 705 holds the die (ingestible sensor microchip) 710, IEM, or sensor pill in place within the capsule 715. This could be at the bottom of the capsule shell on either end, or on the side walls, as shown in the various examples. The conceptualized picture of the three various digitized capsules are shown in FIGS. 7A-7C.

Alternatively, the die could be placed on the bottom of the capsule, upon which a cast material is then filled. The cast material not only functions to hold the die in place, but also functions as a skirt to improve the sensor performance.

The type of glue or casting material could be various hydrogel or other polymeric materials specially formulated to meet desired properties.

The amount of glue or casting material could be varied as part of a manufacturing process that drops a fixed amount into the capsule half shell. Multiple drops of glue could be employed to fix the die, IEM, or sensor pill in place.

Figure 7D:
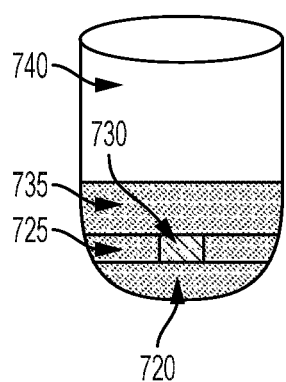

For the casting method, as shown in FIG. 7D as an example, there could be multiple layers casted in a manufacturing process involving different cast materials with the die sandwiched in between. Shown in FIG. 7D is half of a capsule shell 740 with layers at a distal end that include the die 730. Each layer could have a unique function, such as a fast dissolving or disintegrating bottom layer 720, followed by the second skirt layer 725 with the die (IEM or other ingestible sensor) 730 embedded in it, then finally a top layer 735 that protects the sensor (see FIG. 7D). This may be another example of including the IEM or sensor pill to the capsule post-capsule manufacturing, and without requiring a mechanical modification to the existing capsule. Alternatively, the example processes as described and associated with FIGS. 7A-7D may be included during a capsule manufacturing process. For example, the ingestible sensor may be placed inside the capsule and glued or otherwise attached before the drug component is filled into the capsule.

Various Mechanical or Thermo-Mechanical Methods for Attaching Ingestible Sensors to Capsules In some cases, use of forming either mechanically or thermo-mechanical and optionally using adhesives or the thermo-mechanical process to bond the ingestible sensor to the capsule creates a method of integration and securing the ingestible sensor in the capsule.

In some embodiments, an ingestible sensor is inserted in a capsule in such a way with the addition of mechanical or thermo-mechanical methods that can deform parts of the IEM skirt to ensure fit into the capsule. Further, the thermal process can be used attach the ingestible sensor to the capsule.

As an example process for implementing this, an ingestible sensor is inserted in a capsule in such a way with the addition of mechanical or thermo-mechanical methods that can deform parts of the ingestible sensor skirt to ensure fit into the capsule.

Figure 8:
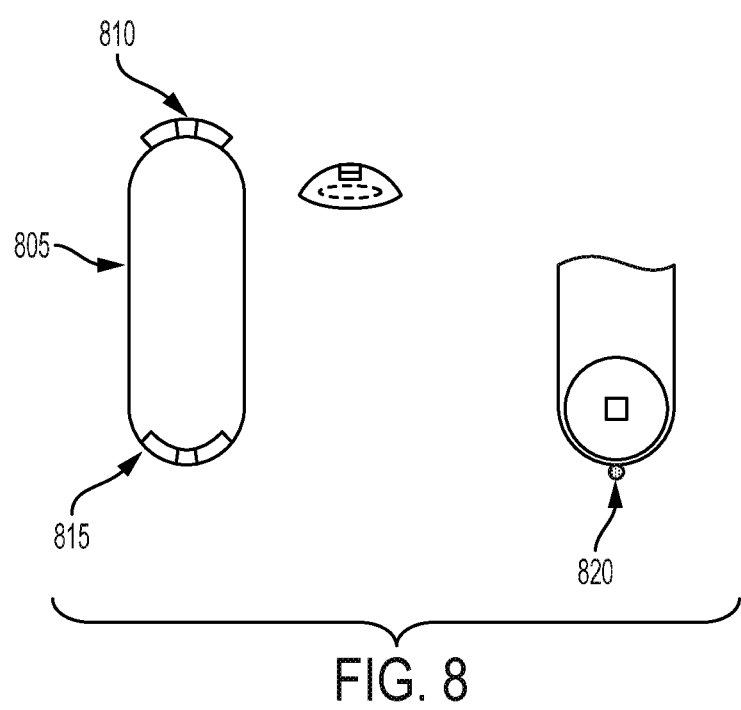
FIG. 8 shows an example illustration for a capsule that includes an ingestible sensor via thermo-mechanical techniques.

Further, the thermal process can be used to attach the ingestible sensor to the capsule. This can be done either on the external or internal surfaces of the drug capsule. This can be implemented either in the end (forming a cone) or along the sides of the capsule (forming an arch). FIG. 8 shows an example illustration for a capsule that includes an ingestible sensor in this way. The capsule 805 shows examples of an IEM 810 formed outside of the capsule, and also and an IEM 815 formed on the inside of the capsule. Notice the curved structure of the skirt portions of the IEMs. In some embodiments, a drop of glue or other adhesive 820 may also be added to aide the process.

Forming could be done against the capsule body, most likely with a forming pin or other support inside the capsule during forming. The forming head would apply heat to the IEM and generally would have the desired matching shape as the location of attachment on the capsule.

Alternately, the capsule attach can be done using an adhesive, such as a small edible glue dot as shown in the lower figures. Glue could be applied either to attach the IEM flat or perpendicular to the surface of the capsule. The latter could be preferred to secure the IEM without adding glue over the electrochemical layers on the circuit.

By employing one of these methods, integration of the ingestible sensor to the capsule is achieved in a method that does not require a priori shaping of the IEM for different capsule types/sizes because the forming can happen at the time of attachment. Also, the glue attach method perpendicular to the capsule edge could secure but also ensure the electrochemical materials are stood clear of the gelatin material to ensure activation. This may be another example of including the IEM or sensor pill to the capsule post-capsule manufacturing, and without requiring a mechanical modification to the existing capsule. Alternatively, the example processes as described and associated with FIGS. 7A-7D may be included during a capsule manufacturing process. For example, the ingestible sensor may be placed inside the capsule and formed onto the capsule wall before the drug component is filled into the capsule.

Ingestible Sensor Beads

In some embodiments, a solution to digitize any existing capsule size, finished encapsulated dose form, may be created by adding an IEM bead to the capsule. A technique called fluid bed coating may be applied to create IEM beads. Fluid bed (FB) coating can coat several functional/nonfunctional material layers over a substrate. The technique is commonly used in pharmaceutical industry to coat excipient substrates (beads).

Figure 9C:
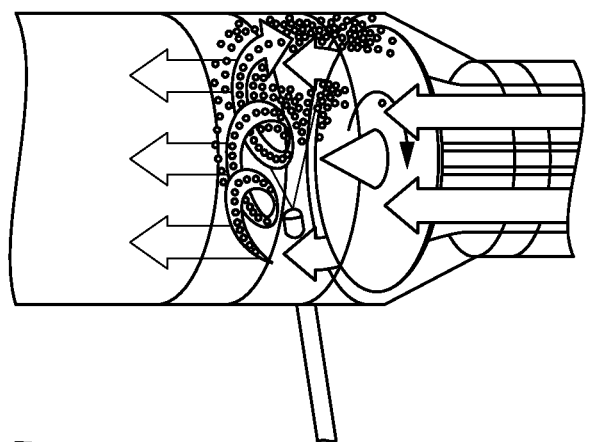
FIGS. 9A-9C show various examples of spray techniques for an ingestible sensor as a microbead in a capsule.
Figure 9B:
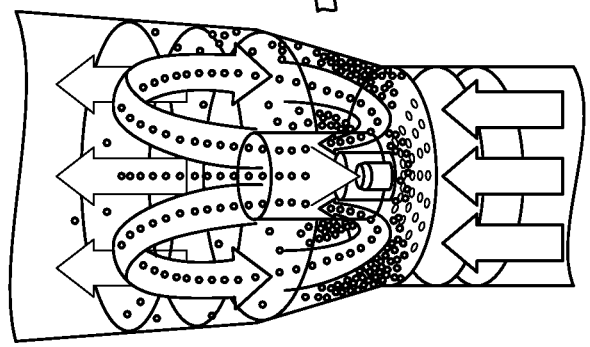
Figure 9A:
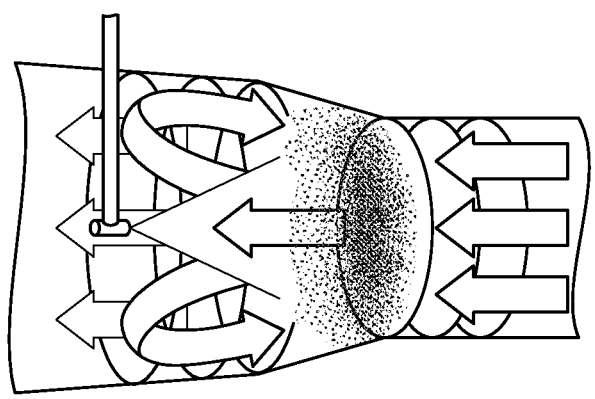

Three variants of spray techniques can be used: Top spray (FIG. 9A); Bottom spray (Wurster Column) (FIG. 9B); and Side spray (FIG. 9C).

Figure 10:
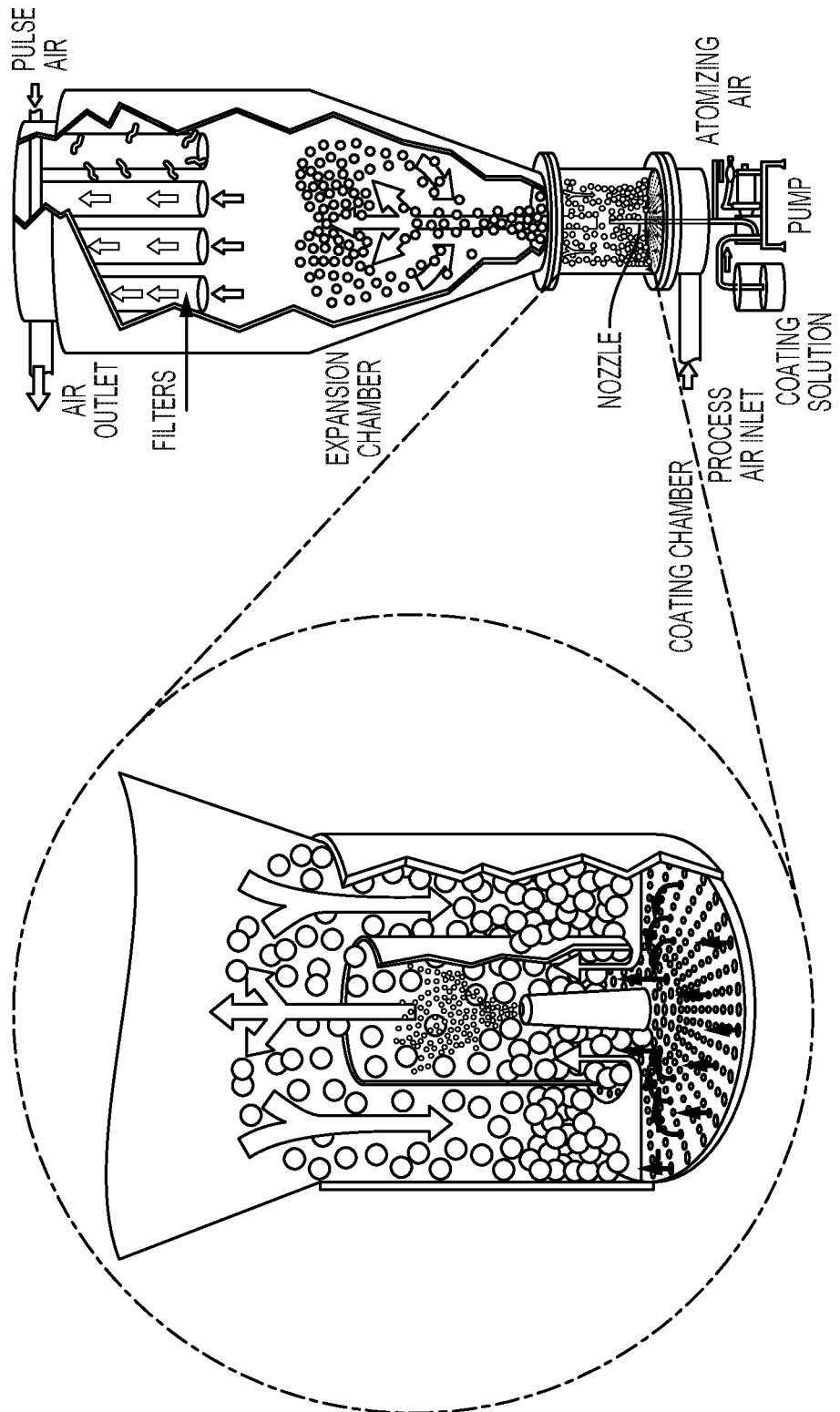
FIG. 10 shows a fluid bed system for the microbead concept.

IEMs (bare without Ethyl Cellulose skirt) or other ingestible sensor microchips can act as a base substrate that can be coated in a fluid bed coater with functional/nonfunctional coating materials to impart specific properties on to the IEM. FIG. 10 of a FB system demonstrates this concept. The coated IEMs (IEM Beads) can then be dropped into a capsule in addition to its drug payload. The IEM bead would be designed to activate soon after it interacts with the gastric fluids, whereas the drug (granules, pellets etc.) can act independent of the IEM as per its intended design.

As one example for employing this method, the base die (ingestible sensor microchip without skirt material) can be obtained from a subset of the current manufacturing process. The base die can then be used in a FB coating system to impart functional/nonfunctional coatings. The coated beads then can be added to multitude of capsule dose forms to establish the proof of concept. This may be another example of including the IEM to the capsule post-capsule manufacturing, and without requiring a mechanical modification to the existing capsule.

Additional Attachment Methods

Figure 11A:
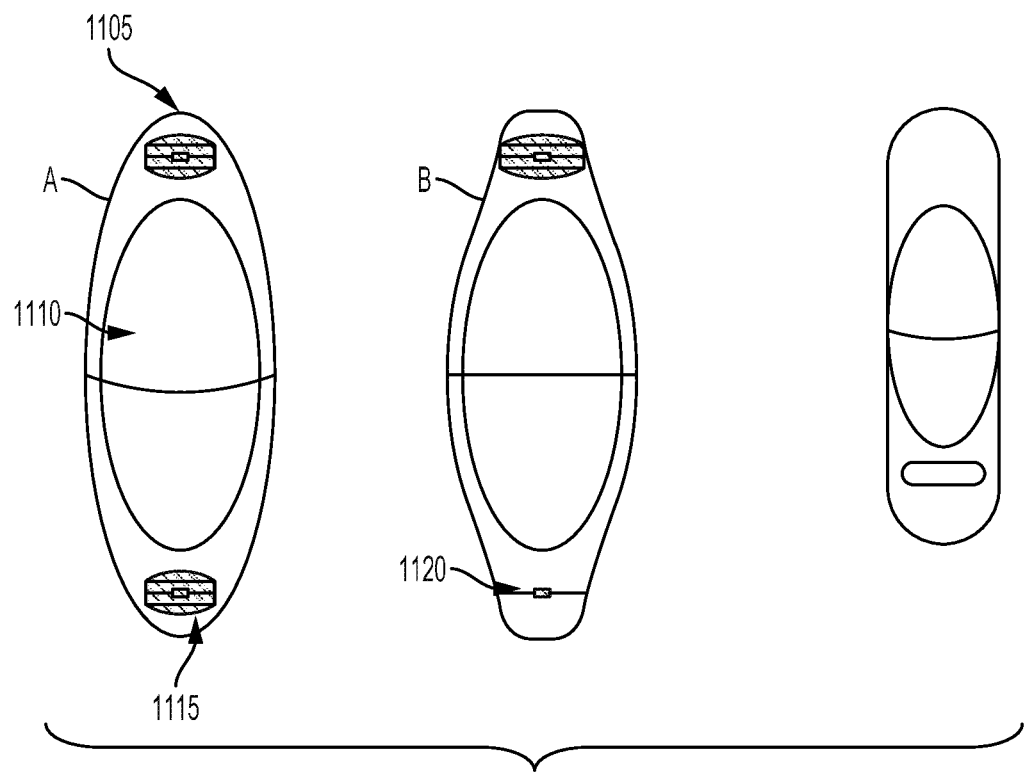
FIGS. 11A-11B provide additional examples of how a sensor pill or tablet can be placed with a drug tablet or other blend during the manufacturing process of the capsule, according to some embodiments.
Figure 11B:
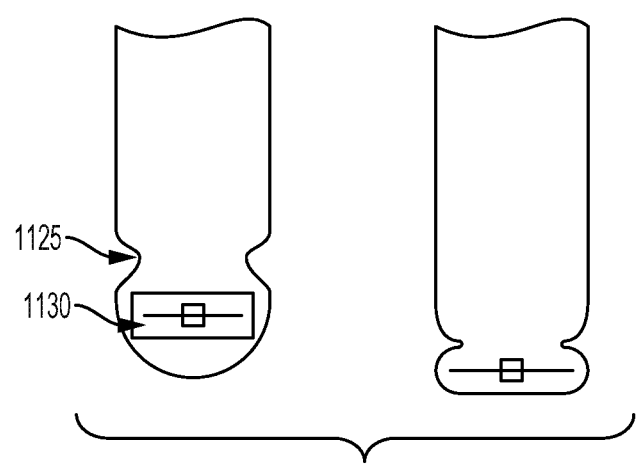

FIGS. 11A and 11B provide additional examples of how a sensor pill or tablet can be placed with a drug tablet or other blend during the manufacturing process of the capsule, according to some embodiments. In FIG. 11A, the drug tablet 1110 is shown in the middle of the capsule material, while two sensor pills or tablets 1105 and 1115 are positioned at the far ends. Tablets 1105 and 1115 are shown, while the IEM 1120 is shown as an alternative example of an ingestible sensor located at a far end of the capsule. The capsule may be manufactured in two pieces first, such as the top half and the bottom half. The sensor pill or tablet may be pre-populated into the far end of the capsule material during the manufacturing process. Then, the drug tablet may be filled in. The two halves may then be connected, either by friction fit, glue, or coated over as some examples.

FIG. 11B shows another example of how the sensor pill or tablet 1130 may be fixed into a far end position of the capsule material during the manufacturing process, according to some embodiments. The capsule material may be formed around the sensor 1130 so as to lock in place the sensor at the far end, as shown. A minor amount of crimping 1125 just around the top of the sensor pill or tablet may be sufficient to secure it to the far end of the capsule material. Then, the drug material may be filled in to the rest of the capsule.

In some embodiments, an ingestible sensor may be applied to a plug that is placed on top of the body of a capsule after being filled. The body of the capsule may include the pharmaceutical agent(s), while the plug fastens the body into the capsule compartment, along with the ingestible sensor. The IEM may break free of the plug upon dissolution of the capsule in the stomach fluid, and may thereby activate. In some embodiments, the sensor pill plug can be attached to a capsule cap that has been formed without a dome at the end or had the dome removed after forming. The attachment method between plug and cap can be friction fit, adhesive attachment, or thermal attachment. Such a cap with sensor pill plug would then be able to be processed on standard capsule filling equipment.

In some embodiments, an on-tablet or on-capsule attachment method is defined using a fast release layer between the IEM and the solid oral drug outer surface and a separate mechanical attachment material. The release layer minimizes interactions between the dissolving drug product materials and the IEM, thus ensuring release and IEM activation, and a separate attachment may be used in addition to the release layer for mechanical strength. The mechanical attachment would typically be external to the release layer but does not need to be. Demonstrated examples include the use of a low melting point lipid covering the active IEM areas as a release layer, and an HPC glue attach around the perimeter for mechanical integrity. A perimeter thermal attachment could also be used with the release layer. The release layer may be a soluble material or may be a meltable lipid, and may be dispensed or printed or placed as a film component. Separation of the materials for mechanical attachment and release allows a more broadly tolerant attachment design independent of the surface or dissolution characteristics of the oral drug product. Various dispense, print, or film patterns for both the release layer and the attachment layer may be used to adjust the properties.

In some embodiments, the disclosed methods may include, where practicable, a skirt material that surrounds the ingestible sensor. This material may be configured to expand during activation. The expansion may behave like a jelly fish expanding in water, or like origami that was originally crumpled or compacted and then is made to expand. In other cases, the skirt may inflate via bubbles that are created upon reaction of the ingestible sensor with the conductive fluid. Other methods of expansion include including layers on the skirt that have different rates of thermal expansion, or different interactions with surface tension of water or other conductive fluid.

In some embodiments, the disclosed methods may include pre-fabricated components that can be attached to various capsule pieces during standard manufacturing processes. For example, modified caps or bands may be manufactured to include an ingestible sensor according to any of the described methods herein, and then these pieces may substitute for the standard capsule components and incorporated into the capsule manufacturing process.

Unless specifically stated otherwise, discussions herein using words such as "processing," "computing," "calculating," "determining," "presenting," "displaying," or the like may refer to actions or processes of a computing device 1100 (e.g., a computer) that manipulates or transforms data represented as physical (e.g., electronic, magnetic, or optical) quantities within one or more memories (e.g., volatile memory, non-volatile memory, or any suitable combination thereof), registers, or other computing device components that receive, store, transmit, or display information. Furthermore, unless specifically stated otherwise, the terms "a" or "an" are herein used, as is common in patent documents, to include one or more than one instance. Finally, as used herein, the conjunction "or" refers to a nonexclusive "or," unless specifically stated otherwise.

Although the flowcharts and methods described herein may describe a specific order of execution, it is understood that the order of execution may differ from that which is described. For example, the order of execution of two or more blocks or steps may be scrambled relative to the order described. Also, two or more blocks or steps may be executed concurrently or with partial concurrence. Further, in some embodiments, one or more of the blocks or steps may be skipped or omitted. It is understood that all such variations are within the scope of the present disclosure.

The present disclosure is illustrative and not limiting. It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. Further modifications will be apparent to one skilled in the art in light of this disclosure and are intended to fall within the scope of the appended claims.

What is claimed is:

1. A method of manufacturing an ingestible capsule including an ingestible sensor, the method comprising:
    partially forming the ingestible capsule using an automated manufacturing process;
    attaching the ingestible sensor to the partially formed ingestible capsule using the automated manufacturing process; and
    completing formation of the ingestible capsule, with the ingestible sensor included, using the automated manufacturing process,
    wherein the ingestible sensor includes a partial power source that powers the ingestible sensor when the partial power source comes into contact with a conductive fluid.

2. The method of claim 1, wherein attaching the ingestible sensor to the partially formed capsule comprises wedging the ingestible sensor into a cap or partially formed body of the capsule, and affixing the ingestible sensor to the cap or partially formed body of the capsule using friction forces between edges of the ingestible sensor and an inner wall of the cap or partially formed body of the capsule.

3. The method of claim 2, wherein the ingestible sensor comprises at least a portion of material that is configured to flex or deform upon applying physical pressure, and wherein wedging the ingestible sensor into the cap or partially formed body of the capsule comprises flexing or deforming at least a portion of the ingestible sensor as the ingestible sensor is wedged into the cap or partially formed body of the capsule.

4. The method of claim 1, wherein:
    partially forming the ingestible capsule comprises partially shaping capsule material using a forming pin;
    attaching the ingestible sensor to the partially formed capsule comprises:
        placing the ingestible sensor on a tip of the forming pin; and
        embedding the ingestible sensor into a rounded end of the partially formed capsule using the tip of the forming pin; and
    completing formation of the ingestible capsule comprises applying additional capsule material over the forming pin such that the ingestible sensor is attached via at least one surface of the additional capsule material that is not masked by the forming pin.

5. The method of claim 4, wherein the ingestible sensor comprises a mating surface positioned opposite a side of the ingestible sensor adjacent to the rounded end of the capsule, the mating surface configured to mate with a drug component to be filled into the capsule.

6. The method of claim 5, wherein the mating surface of the ingestible sensor comprises a concave shape.

7. The method of claim 5, wherein the mating surface of the ingestible sensor comprises two straight edges connected at an acute angle.

8. The method of claim 1, wherein attaching the ingestible sensor to the partially formed capsule comprises:
    coating a side of the ingestible sensor facing a distal end of the partially formed capsule with a material configured to accelerate separation of the ingestible sensor from the distal end of the capsule when the ingestible sensor is exposed to a fluid.

9. The method of claim 1, wherein a portion of the capsule is constructed to be insoluble such that, when the capsule dissolves in a fluid, the insoluble portion of the capsule remains attached to the ingestible sensor and creates a skirt around the ingestible sensor.

10. The method of claim 1, wherein attaching the ingestible sensor to the partially formed ingestible capsule using the automated manufacturing process comprises:
    casting a fast disintegrating layer of material into a distal end of the partially formed ingestible capsule;
    embedding the ingestible sensor onto the fast disintegrating layer of material;
    casting an insoluble layer of material onto the fast disintegrating layer and around the ingestible sensor; and
    casting a protective layer of material onto the insoluble layer and the ingestible sensor.

11. The method of claim 1, wherein:
    attaching the ingestible sensor to the partially formed capsule comprises:
        placing the ingestible sensor in a distal portion of the partially formed capsule; and
    completing formation of the ingestible capsule comprises crimping the partially formed capsule around the ingestible sensor such that the ingestible sensor is securely fastened within the distal portion of the capsule.

\* \* \* \* \*